US00PP25855P3

(12) United States Plant Patent
Pavlich

(10) Patent No.: US PP25,855 P3
(45) Date of Patent: Sep. 1, 2015

(54) ***BEGONIA* PLANT NAMED 'AURORA'**

(50) Latin Name: *Begonia rex-cultorum*
Varietal Denomination: Aurora

(71) Applicant: Terra Nova Nurseries, Inc., Canby, OR (US)

(72) Inventor: John C. Pavlich, East Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 182 days.

(21) Appl. No.: 13/987,233

(22) Filed: Jul. 12, 2013

(65) Prior Publication Data

US 2015/0020266 P1 Jan. 15, 2015

(51) Int. Cl.
*A01H 5/12* (2006.01)

(52) U.S. Cl.
USPC ..... Plt./343

(58) Field of Classification Search
USPC ..... Plt./343
See application file for complete search history.

(56) References Cited

PUBLICATIONS

Greenhouse Management. Two new varieties available from Terra Nova Nurseries, Feb. 12, 2013, retreived on Feb. 26, 2013, retrieved from the Internet at <http://www.greenhousemag.com/terra-nova-sneak-peek-2013.aspx> 2pp.*

Upov Pluto Plt Variety Database 20150306, retrieved on Mar. 9, 2015, retrieved from the Internet at <https://www3.wipo.int/pluto/user/en/index.jsp>, one page.*

* cited by examiner

*Primary Examiner* — June Hwu
(74) *Attorney, Agent, or Firm* — Klarquist Sparkman, LLP

(57) ABSTRACT

A new and distinct form of *Begonia* plant characterized by broad leaves colored silver with a dark star-shape at the leaf base that is surrounded by a purple blush, maroon leaf backs, a bushy habit, tolerant of cool temperatures to 33° F., and excellent vigor.

1 Drawing Sheet

Botanical denomination: *Begonia rex-cultorum.*
Variety designation: 'Aurora'.

BACKGROUND OF THE INVENTION

The present invention relates to a new and distinct cultivar of *Begonia*, of the family Begoniaceae, and given the cultivar name 'Aurora'. The new cultivar originated from a cross between *Begonia* 'Shaun Henthorne', an unpatented Rex type as the seed parent and an unnamed, unpatented Angelwing type, as the pollen parent. This selection is uniquely characterized by:

1. iridescent blue silver angelwing-shaped leaves that display rose purple in the leaf center and as a border on the margin,
2. maroon and green leaf backs,
3. a bushy habit,
4. tolerant of cool temperatures to 33° F., and
5. excellent vigor.

Compared to *Begonia* 'Shaun Henthorne', an unpatented plant and the seed parent, the new cultivar has leaves that ovate with oblique and cordate base rather than broadly ovate with an oblique swirling base. In addition the foliage color of the new cultivar is much more muted and silver and the plant survives better in the cold.

Compared to the unnamed *Begonia* Angelwing pollen parent, the new cultivar has leaves that are colored silver with rose purple markings rather than green with a few silver spots. The Angelwing was an upright, cane-type while the new cultivar has a bushy habit with fibrous roots.

Compared to *Begonia* 'Roseburg', an unpatented plant, the new cultivar has smaller leaves, more overlapping leaf bases, more silver leaf color, and a more basal crown habit.

The new variety has been reproduced only by asexual propagation (cuttings and tissue culture). Each of the progeny exhibits identical characteristics to the original plant. Asexual propagation by micropropagation using the meristem as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows the foliage and habit of *Begonia* 'Aurora' in August in Canby, Oreg.

DETAILED PLANT DESCRIPTION

The following is a detailed description of the new *Begonia* cultivar based on observations of ten-month-old specimens grown in one gallon containers in a cool greenhouse in early March in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The Royal Horticultural Society Colour Chart, 5$^{th}$ edition, 2007.

Plant:

*Type*.—Herbaceous perennial, fibrous *Begonia*.

*Form*.—Clumping, caulescent.

*Cold hardiness*.—USDA Zone 10a.

*Size*.—grows to 28 cm tall and 50 cm wide.

*Vigor*.—Excellent.

Stem:

*Type*.—Upright.

*Size*.—Grows to 7 cm long and 18 mm wide.

*Internodes*.—From 3 mm to 2.5 cm long.

*Surface*.—Glabrous.

*Color*.—Greyed Purple 187A on young stems to Brown N200A on older stems.

Leaf:

*Type*.—Simple.

*Arrangement*.—Alternate, often congested on very short internodes.

*Shape*.—Ovate.

*Margins*.—Slightly undulate, coarsely serrate.

*Apex*.—Acuminate.

*Base*.—Oblique, overlapping.

*Venation*.—Palmate, color topside between Greyed Green 197A and Yellow Green 152A, bottom side Greyed Purple 187A.

*Blade size*.—Grows to 10 cm wide and 17.5 cm long.

*Surface texture*.—Sparsely pubescent on top and bottom.

*Stipules*.—Deciduous, ovate-lanceolate, 17 mm long and 10 mm wide, apex acuminate and cuspidate, entire, both sides glabrous and Greyed Red 181A.

*Petiole description*.—Grows to 25 cm long and 6 mm wide, succulent, glabrous, between Greyed Green 197A and Yellow Green 152A.

*Leaf color*.—Top side closest to Greyed Green 189B where silver, tinted Purple N79B in the leaf center and on the outside 1 cm of the leaf; bottom side Greyed Purple 187A along the veins and leaf margin, Green 138B interveinally.

Inflorescence:

*Type*.—Axillary, bisexual, cymose.

*Number of flowers per cyme*.—3 to 4.

*Peduncle description*.—Grows about 5 cm long and 2.5 mm wide, succulent, glabrous, between Greyed Green 197A and Yellow Green 152A; with 2 opposite, dehiscent petiolate leaf-bracts below each cyme, which grow to 7 mm wide and 14 mm long, margins entire, tip apiculate, both sides glabrous and Greyed Red 181D.

*Pedicel description*.—Grow to 15 mm long, 1 mm wide, glabrous, Yellow Green 146D.

*Bloom period*.—Early spring in Canby, Oreg.

Flower bud:

*Size*.—Staminate flowers 12 mm long and 10 mm wide prior to opening; pistillate flowers are 15 mm deep and 15 mm wide prior to opening.

*Description*.—Ovoid, sparsely pubescent.

*Color*.—Greyed Red 151C on tepal area, ovary Greyed Red 151C darkening to Greyed Purple 183C.

Flower:

*Type*.—Monoecious, bilaterally symmetrical.

*Pistillate flower*.—None seen.

*Staminate flower*.—7 mm deep and 22 mm wide, 4 tepals, 2 larger outer tepals 15 mm long and 15 mm wide, cupped, broadly elliptical, margin entire, tip obtuse, base truncate, inside Red Purple 63D in center to 65D on sides and outside 58D in center and 65D on sides; inner tepals grow to 12 mm long and 8 mm wide, oblong, entire, tip obtuse, base attenuate, both sides Red Purple 65D with a band of pink in center, 63D outside and 65D inside; stamen many in a globular head 8 mm in diameter, filament 2 mm long, anthers 1.5 mm long and Yellow 7A, no pollen, male sterile.

*Fragrance*.—None.

*Lastingness*.—A cyme blooms for about 4 weeks on the plant.

Fruit and seed: None, sterile.

Diseases and pests: The new cultivar is typical to the genus. No known resistances to pests or diseases. No problems have been found in Canby, Oreg.

I claim:

1. A new and distinct form of *Begonia* plant as hereby illustrated and described.

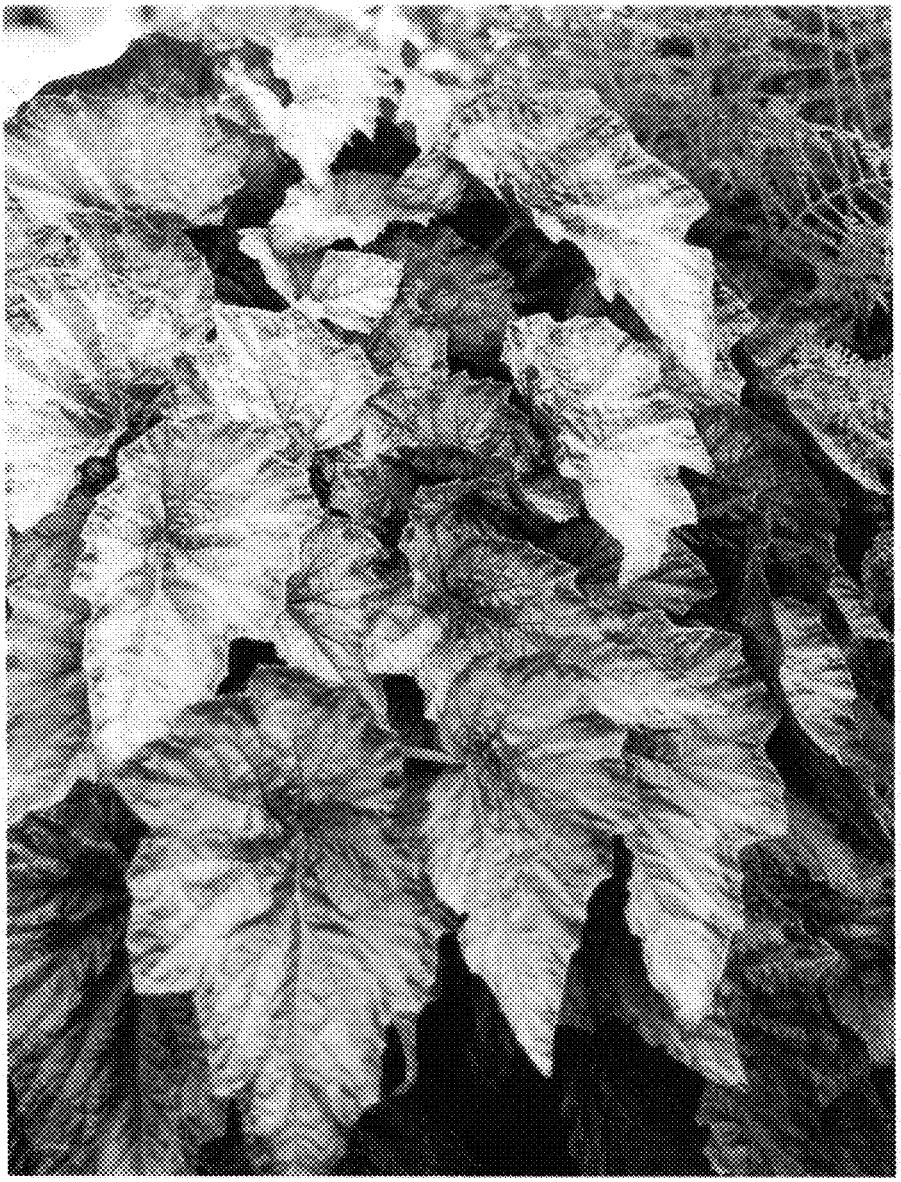

* * * * *